United States Patent
Brinton

(10) Patent No.: US 11,071,977 B2
(45) Date of Patent: Jul. 27, 2021

(54) BIOLOGICAL SAMPLE ANALYSIS DEVICE

(71) Applicant: William Brinton, Mt. Vernon, ME (US)

(72) Inventor: William Brinton, Mt. Vernon, ME (US)

(*) Notice: Subject to any disclaimer, the term of this patent is extended or adjusted under 35 U.S.C. 154(b) by 0 days.

(21) Appl. No.: 15/918,621

(22) Filed: Mar. 12, 2018

(65) Prior Publication Data

US 2018/0257068 A1    Sep. 13, 2018

Related U.S. Application Data

(60) Provisional application No. 62/470,650, filed on Mar. 13, 2017.

(51) Int. Cl.
| | | |
|---|---|---|
| *B01L 3/00* | (2006.01) | |
| *G01N 33/00* | (2006.01) | |
| *G01N 21/75* | (2006.01) | |
| *G01N 21/3504* | (2014.01) | |
| *G01N 21/84* | (2006.01) | |

(52) U.S. Cl.
CPC ............... *B01L 3/50* (2013.01); *B01L 3/508* (2013.01); *G01N 21/3504* (2013.01); *G01N 21/75* (2013.01); *G01N 33/0004* (2013.01); *B01L 2200/18* (2013.01); *B01L 2300/027* (2013.01); *B01L 2300/042* (2013.01); *B01L 2300/046* (2013.01); *B01L 2300/0627* (2013.01); *B01L 2300/0832* (2013.01); *B01L 2300/0851* (2013.01); *G01N 2021/8466* (2013.01)

(58) Field of Classification Search
None
See application file for complete search history.

(56) References Cited

U.S. PATENT DOCUMENTS

| | | | | |
|---|---|---|---|---|
| 4,220,715 A | * | 9/1980 | Ahnell | C12Q 1/04 435/287.1 |
| 4,955,946 A | | 9/1990 | Mount et al. | |
| 5,038,040 A | | 8/1991 | Funk et al. | |
| 5,155,019 A | * | 10/1992 | Sussman | C12M 41/34 250/343 |
| 5,232,839 A | * | 8/1993 | Eden | C12M 41/46 435/287.4 |
| 5,770,153 A | * | 6/1998 | Wagner | G01N 7/00 422/79 |
| 6,598,458 B1 | * | 7/2003 | Edwards | G01N 1/2294 166/264 |
| 6,903,823 B1 | * | 6/2005 | Muller | G01N 21/03 356/437 |
| 2009/0301234 A1 | | 12/2009 | Risk | |
| 2011/0061442 A1 | * | 3/2011 | Furtaw | G01F 22/02 73/23.2 |
| 2011/0068940 A1 | * | 3/2011 | Kim | G01N 1/22 340/632 |
| 2015/0110677 A1 | * | 4/2015 | Rajasekharan | B01L 3/502 422/82.09 |

FOREIGN PATENT DOCUMENTS

CN          205786302 U       12/2016

* cited by examiner

*Primary Examiner* — Matthew D Krcha
(74) *Attorney, Agent, or Firm* — Jeffrey Joyce, Esq.

(57) ABSTRACT

A biological sample analysis device that is an easily portable free-standing device for determining the rate of deterioration of biological samples.

7 Claims, 5 Drawing Sheets

BIOLOGICAL SAMPLE ANALYSIS DEVICE

FIELD OF THE INVENTION

The invention relates to devices that are used for testing the rate of deterioration of biological samples such as soil and compost.

DISCUSSION OF PRIOR ART

The rate at which biological samples such as soil and compost deteriorate is of critical importance to a wide array of sciences. Soil respiration, for example, is a key ecosystem process that is of particular interest and importance to soil scientists, ecologists, and farmers. The amount of soil respiration that occurs in an ecosystem is controlled by a number of factors, such as temperature, moisture, nutrient content and level of oxygen in the soil. It is of significant importance to a number of industries, particularly those related to agriculture as soil provides the environment for plant growth and the quality of the soil is vital to successful and sustainable farming.

Different methods exist for measuring rates of deterioration, however, all are cumbersome and, in varying manners, inconvenient. For example, a flux chamber is a common soil respiration testing device, but it is large and very difficult to move from one testing site to another. Other devices, such as SOLVITA detector gels, DRAEGER-TUBE chemical reagent tubes, and other hand-held carbon dioxide ($CO_2$) devices are smaller devices that measure $CO_2$ deterioration but do not also collect, store and interpret data in a single unit. The smaller units also, generally, require that at least some part of the test kit be discarded after each use.

What is needed, therefore, is a free-standing portable reusable biological sample collection and analysis device.

BRIEF SUMMARY OF THE INVENTION

The inventive device is biological sample analysis device that is an easily portable, reusable, free-standing device for determining the rate of deterioration of biological samples, and in particular the rate of carbon dioxide ($CO_2$) respiration. More specifically, the device allows for a test sample to be placed inside a relatively small enclosure and, after a suitable incubation time, such as 24 hours, analyzes the rate of deterioration by, for example, converting the accumulated data to a standard biological $CO_2$ rate. After a test is completed the sample may be discarded, the enclosure cleaned, and a subsequent test run on a different sample using the same device. The device includes two primary components: a gas-tight enclosure for incubation of a conventional quantity of a sample; and, a data collection and analysis unit that captures and analyzes relevant biological data.

The data collection and analysis unit includes a conventional infrared ("IR") sensor that detects gas emissions, such as, for example, carbon dioxide, methane, ammonia, or oxygen. The IR device is coupled to a computer microchip preprogrammed to continuously evaluate the data using conventional means and known techniques in order to prepare an analysis report. The data collection and analysis unit has two functional capabilities; one is to continuously display data via a self-contained light-emitting diode ("LED") screen, enabling the entire unit to be used as a self-standing measurement device in a manual mode; the second is to connect to any suitable computing device, such as a desktop computer, laptop or tablet, via an conventional interface such as a universal serial bus ("USB") cable, so as to allow for user inputs and to automatically upload results and enable data interpretation over time periods that are common for biological studies, such as for 0-24 hours, 24-48 hours and 48-72 hours.

The biological samples, such as, for example, soil, compost, or oilseeds and grains are placed in the gas-tight enclosure that is then sealed by a lid having a connection to the data collection and analysis unit, and after a suitable period of time the device is able to summarize the data and convert it to appropriate units of carbon emission and to report respiration per unit of mass of sample placed into the gas-tight enclosure.

The data collection and analysis unit may be built into a cover or lid of the gas-tight enclosure, or it may be a separate device that is connectable to the gas-tight enclosure's cover by hoses or tubes that allow the gas to pass from the gas-tight enclosure to the data collection and analysis unit. In either case, the gas-tight enclosure's cover may include air-tight accessible sample ports through which additional gases, for example oxygen, may be injected, or samples withdrawn for other forms of analyses. Air-tight gas lines may be affixed to the sample ports along with a suitable and conventional gas flow-rate monitor so that the rate of accumulation inside the flask is held constant and thusly the rate of deterioration may be calculated as the mass of air flow corrected to Ideal Gas Law quantities times the $CO_2$ concentration indicated on the data collection and analysis unit.

BRIEF DESCRIPTION OF THE DRAWINGS

The present invention is described with reference to the accompanying drawings. In the drawings, like reference numbers indicate identical or functionally similar elements. The drawings are not drawn to scale.

DETAILED DESCRIPTION OF THE INVENTION

Figure 1:
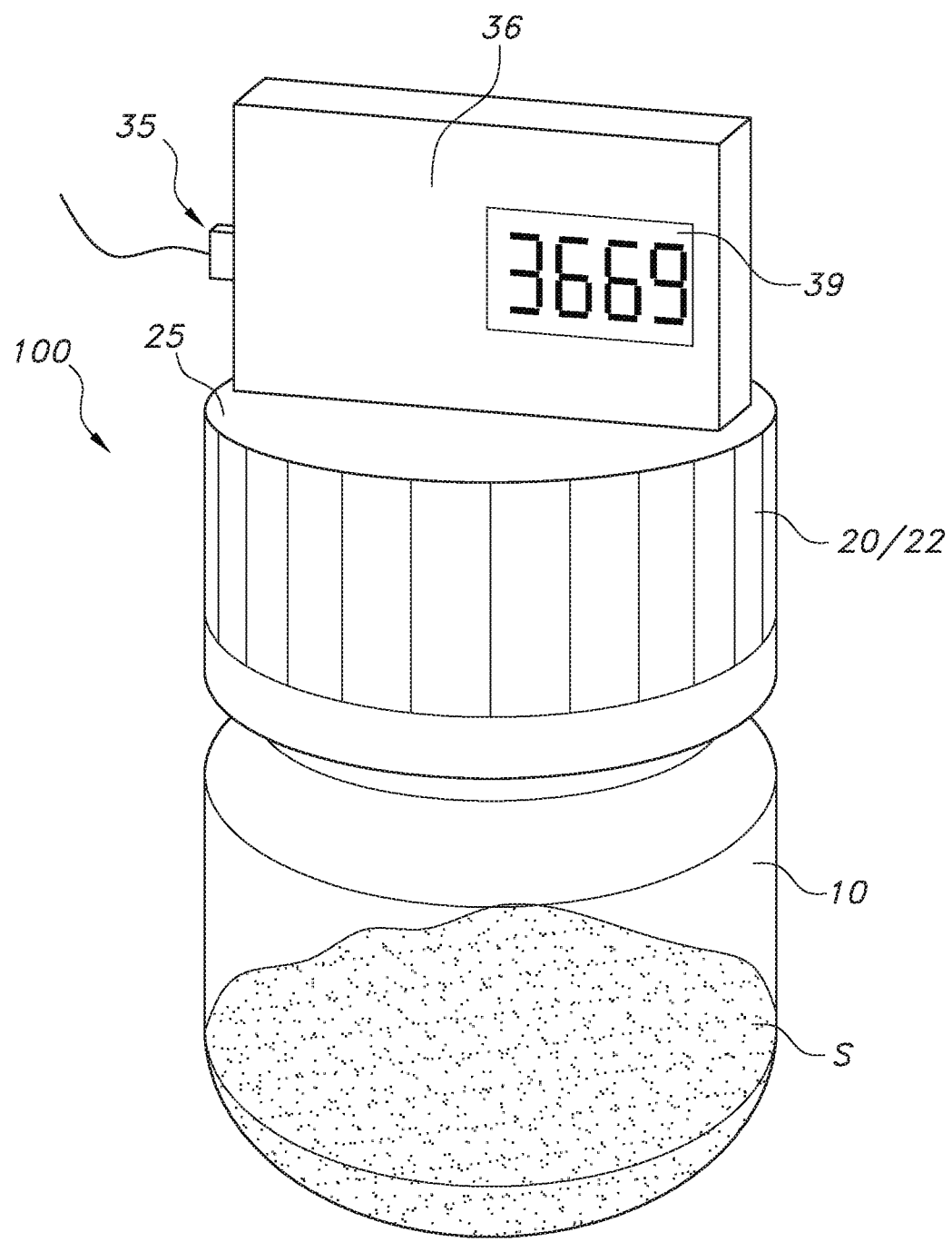
FIG. 1 is a front view of the fully assembled device according to the invention.

The present invention will now be described more fully in detail with reference to the accompanying drawings, in which the preferred embodiments of the invention are shown. This invention should not, however, be construed as limited to the embodiments set forth herein; rather, they are provided so that this disclosure will be complete and will fully convey the scope of the invention to those skilled in the art.

FIGS. 1-7 illustrate a first embodiment of a biological sample analysis device 100 according to the invention, including a biological sample chamber 10 and a data collection and analysis unit 20. In this embodiment, the data collection and analysis unit 20 is integrated into a cover 22 to the biological sample chamber. A conventional amount of a biological sample S is placed inside the biological sample chamber 10, and the data collection and analysis unit 20 is secured to the top of the biological sample chamber 10 creating a gas-tight enclosure. The data collection and analysis unit 20 senses the gas emissions from the sample, calculates the rate of deterioration, and displays that relevant data to a user. After a test is completed the biological sample S may be discarded, the biological sample chamber 10 cleaned, and a subsequent test run on a different biological sample.

Together, the biological sample chamber 10 and data collection and analysis unit 20 are of a relatively small size such that the device 100 is easily portable and free-standing. For example, a biological sample chamber 10 that is cylindrical in shape and that has a volume in the range of approximately 450 cubic centimeters to approximately 1 liter is reasonable. The biological sample analysis device 100 also accommodates a wide range of biological sample S sizes; for example, a device 100 having a biological sample chamber 10 with a volume of roughly 1 liter is able to accommodate a biological sample ranging in mass from approximately 5 grams to approximately 500 grams.

The rate of deterioration, which also may be called carbon dioxide ("CO2") respiration or, simply, CO2 respiration, may be represented severally as the change in atmospheric CO2 inside the biological sample chamber 10 or converted via the Ideal Gas Law to a mass of CO2 milligrams ("mg") which may be divided into the sample rate for a relative decay rate. Relative decay may be represented in the device as mg CO2/kilograms ("kg") of sample, or reduced to mg CO2-C, as carbon, equivalent to sample weight times the carbon content. The difference between the starting weight in total carbon of the sample and the atmospheric CO2 converted via the Ideal Gas Law to mass is therefore the amount of decay, deterioration or respiration the sample has undergone in a period of time.

The biological sample chamber 10 is a gas-tight enclosure, such as a glass jar. The data collection and analysis unit 20 includes a number of components that detect the gas emission data, analyzes the gas emission data, and displays results, i.e. the rate of deterioration, to the user. More specifically, the data collection and analysis unit 20 is integrated into the cover 22, the cover having a bottom side 23 that includes a gas emissions sensing unit 27 and a top side 25 that includes a data analysis and display unit 36 for calculating and displaying pertinent data, such as the rate of deterioration.

Figure 2:
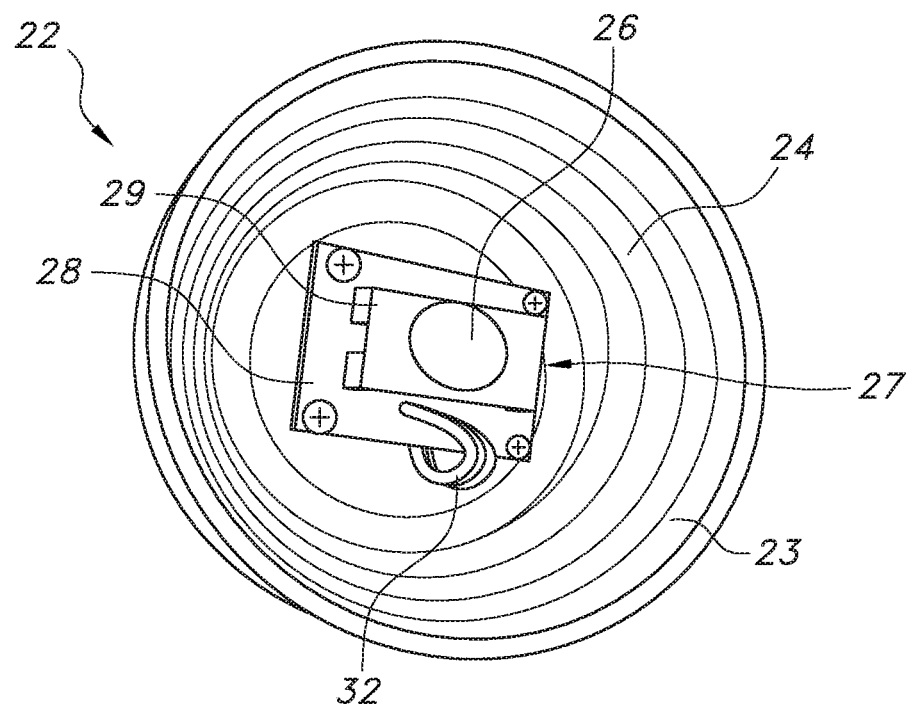
FIG. 2 is top view showing the inside of the data collection and analysis unit.
Figure 3:
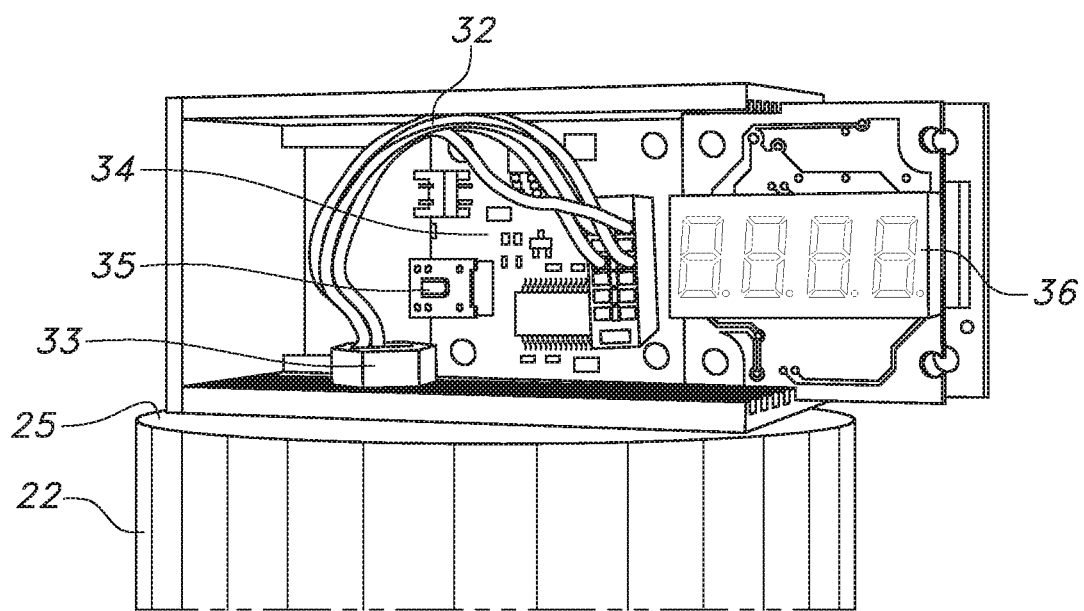
FIG. 3 is a front view of the LED display without the faceplate.
Figure 4:
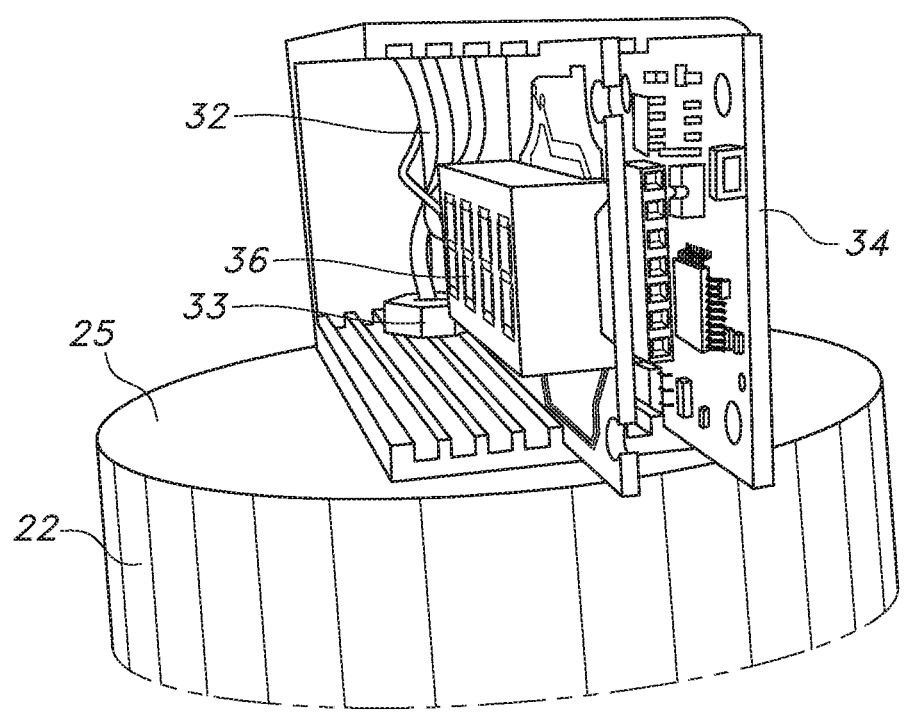
FIG. 4 is a side view of the LED display.

The gas emissions sensing unit 27 includes an Infrared ("IR") sensor 26, best illustrated in FIG. 2, that is coupled to a sensor circuit board 28. The sensor 26 may be any sensor that is capable of detecting gas emissions such as carbon dioxide, methane, ammonia, or oxygen. For example, the TELAIRE T6713 CO2 sensor and the CO2METER SPRINTIR sensor are suitable nondispersive infrared (NDIR) CO2 sensors. Preferably, the sensor 26 is suited for battery operation and requires ultra-low power, such as 3.5 milliwatts (mW), and uses a non-dispersive infrared absorption sensing method. The sensor circuit board 28 is a conventional circuit board that has a programmable microprocessor 29 that is capable of receiving input from an IR sensor, for example, a BS2PE, or a PROPELLER P8X32A SPIN from PARALLAX INC, or a RASPBERRY PI 3 from ADAFRUIT INDUSTRIES, LLC. The sensor 26 detects the gas emissions data and sends data signals relaying the gas emissions data to the programmable microprocessor 29. These types of programmable microprocessors are devices that typically have their own developmental toolkits that allow programmers to control the software and hardware on the programmable microprocessor 29 using conventional programming techniques.

The sensor circuit board 28 connects to one or more wires 32 that extend through a gas-tight opening 33 in the cover 22 and connect to the data analysis and display unit 36. The data analysis and display unit 36 includes a display and analysis circuit board 34, best shown in FIGS. 3 and 4, which is a conventional programmable logic board. The display and analysis circuit board 34, as with the programmable microprocessor 29, is the type of programmable logic board that typically has its own developmental toolkit that allows programmers to control the software and hardware on the programmable logic board/display and analysis circuit board 34 using conventional programming techniques. There are a number of suitable programmable logic boards such as, for example, the PROPELLER FLIP Microcontroller made by PARALLAX.

The display and analysis circuit board 34 also has an external communication link 35, such as a universal serial bus ("USB") port or a Power over Ethernet ("POE") system, that allows the user to connect the biological sample analysis device 100 to the user interface device (not shown) such as a computer, smart phone or tablet, by a cable or wireless signal for transferring additional data inputs and outputs between the user to the data collection and analysis unit 20. This link 35 may also serve as a connection to a power source for the biological sample analysis device 100 by conveying electricity from the user interface device or by being directly connected to an electrical outlet using conventional means such as, for example, a USB cable.

More specifically, the display and analysis circuit board 34 is programmed using conventional techniques to receive sensor data from the sensor circuit board 28, accept input from the user through the user interface device, such as the weight of the sample and volume of the biological sample chamber 10. Based on these inputs, the display and analysis circuit board 34 calculates the concentration of CO2 gas and from this the rate of sample deterioration. A display 39 mounted in the data analysis and display unit 36 displays data, such as the rate of deterioration, to the user. In the embodiment shown, the display 39 is a display that uses an array of light-emitting diodes ("LEDs") as pixels for a video display. Any form of display with suitable units for alpha-numeric characters is suitable for use with the device 100.

Figure 5:
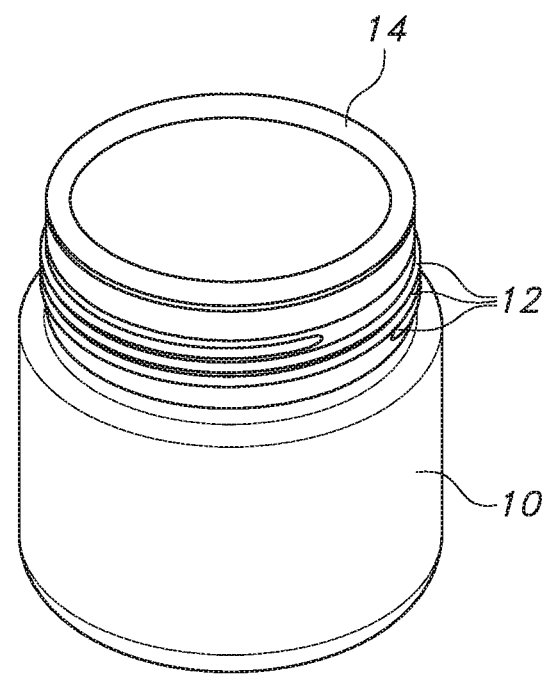
FIG. 5 is a side view of the biological sample chamber showing the ridges.

The bottom side of the cover 22 has a suitable number of ridges 24, for example five ridges 24 are included in the embodiment shown, that work in conjunction with an approximately corresponding number of ridges 12, shown in FIG. 5, on the top of the biological sample chamber 10 so as to allow the cover 22 to be screwed onto the biological sample chamber 10 in a manner that creates a gas-tight seal. A rubber seal 14 is also included to help create a gas-tight seal to prevent the entrance or loss of CO2 or other gases normally present inside and outside the biological sample chamber 10.

Figure 7:
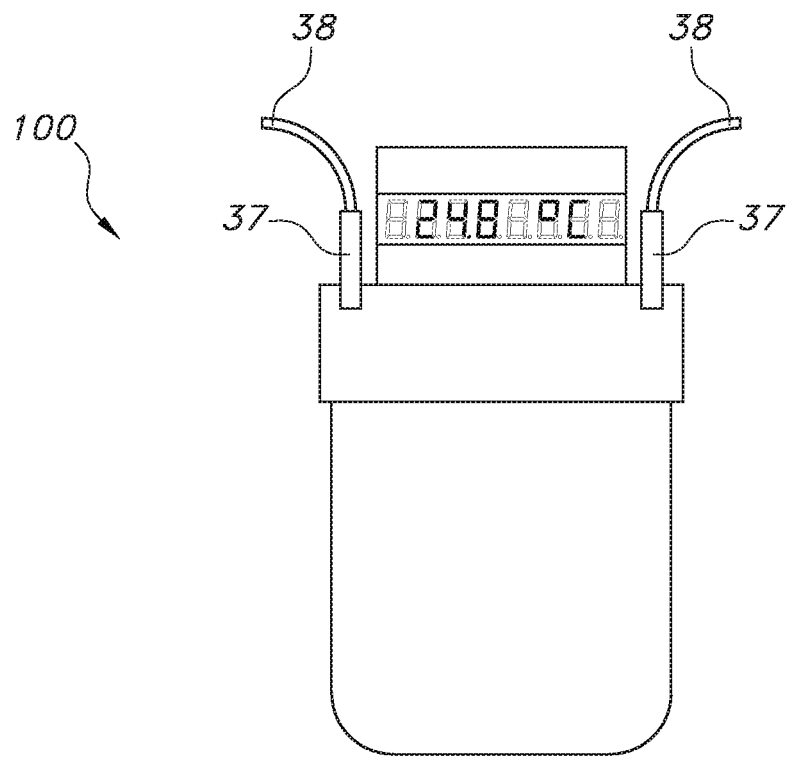
FIG. 7 is a front view of the device having gas lines.

The cover 22 may also include air-tight accessible sample ports 37, shown in FIG. 7, through which additional gases, for example oxygen, may be injected, or samples withdrawn for other forms of analyses. Air-tight gas lines 38 may be affixed to the sample ports along with a suitable gas flow-rate monitor so that the rate of accumulation inside the biological sample chamber 10 is held constant and thusly the rate of deterioration may be calculated as the mass of air flow corrected to Ideal Gas Law quantities times the CO2 concentration.

Figure 6:
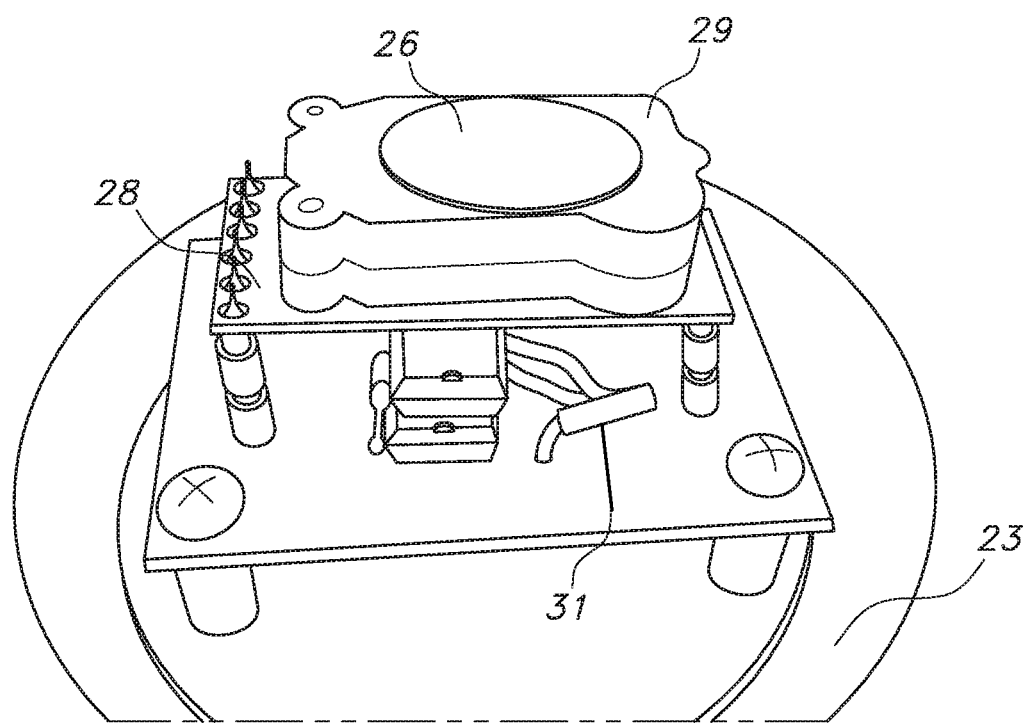
FIG. 6 is a side view of the circuit board showing the temperature sensor.

Also attached to the sensor circuit board 28 is a temperature sensor 31, shown in FIG. 6, which detects the temperature inside of the chamber 10 and relays the temperature inside the chamber 10 to the programmable microprocessor 29. The temperature sensor 31 aids calculations via the Ideal Gas Law of the mass of molecules present. More specifically, the Ideal Gas Law states that a quantity of gas is determined by its pressure, volume, and temperature. The current form controls pressure in the sealed system therefore the equation employed in the sensor circuit board relates these in two forms. The temperature used in the equation is an absolute temperature: the appropriate International System of Units ("SI unit") is the kelvin, calculated based on Celsius readings on the temperature sensor 31.

Figure 8:
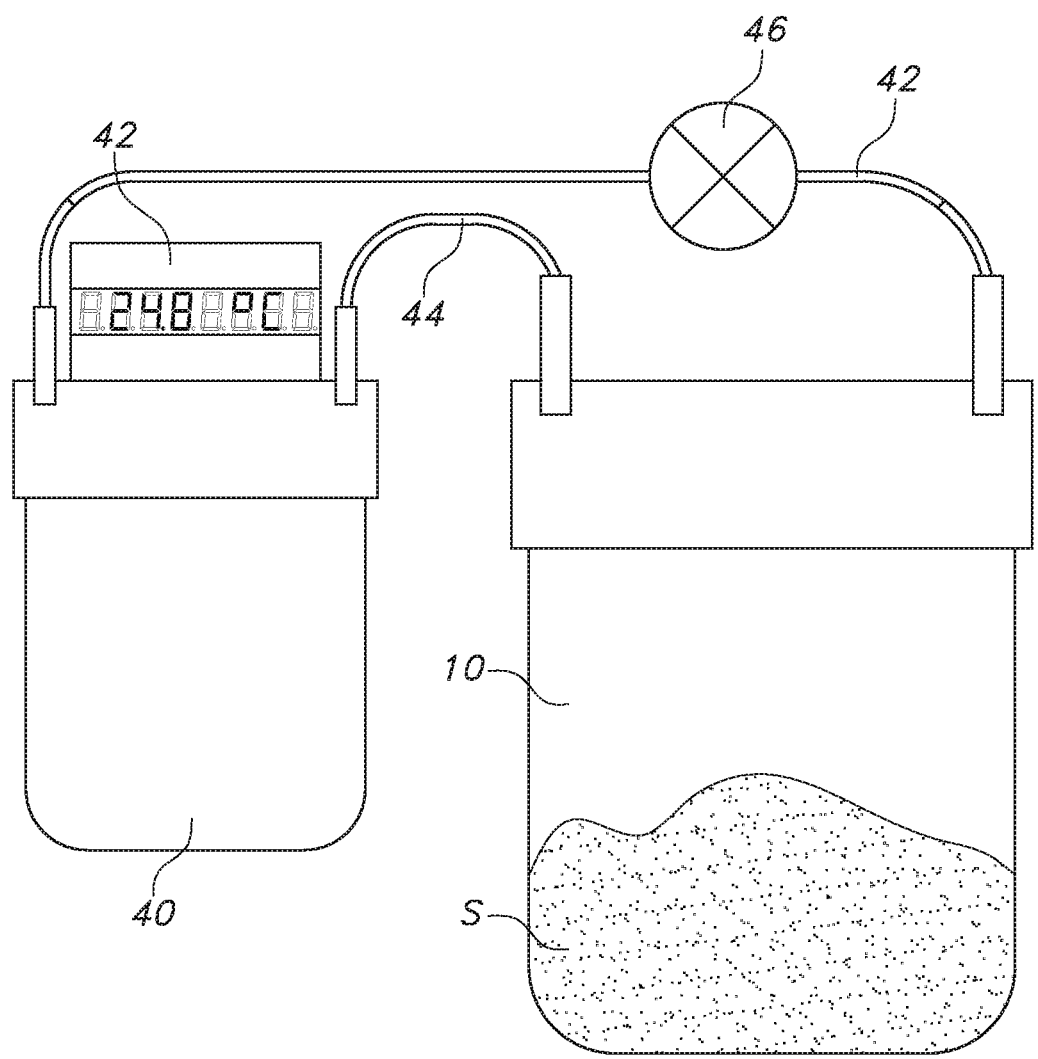
FIG. 8 is a front view of a second embodiment having a separate analysis chamber and sample chamber.

FIG. 8 shows a second embodiment where the data collection and analysis unit 20 is not a cover that is attached directly to the biological sample chamber 10 but is a separate detached unit that is employed with a reading chamber 40. The components of the data collection and analysis unit 20 are the same, however, an air inflow tube 42 and an air outflow tube 44 are used to connect the reading chamber 40 to the biological sample chamber 10. An air movement device 46, such as a peristaltic pump, is used to displace air from the biological sample chamber 10 to the reading chamber 40 in order to reach equilibrium between the two chambers 10, 40. The total air volume of both systems is input into the data collection and analysis unit 20, which enables correct calculation of the rate of deterioration or respiration of the biological sample in the remote container. In this embodiment the rate of flow of the air movement device 46 does not need to be known as the system reaches equilibrium after a short period of time and is calculable.

It is understood that the embodiments described herein are merely illustrative of the present invention. Variations in the construction of the biological sample analysis device may be contemplated by one skilled in the art without limiting the intended scope of the invention herein disclosed and as defined by the following claims.

What is claimed is:

1. A portable reusable biological sample analysis device adapted to analyze one or more biological samples, the device comprising:
   a biological sample chamber that consists of a floor and a sidewall, together the floor and the sidewall forming a container having an open top and an inner space, the one or more biological samples contained within the inner space;
   a data collection and analysis unit that is a cover for the biological sample chamber and is directly affixable to the biological sample chamber, the data collection and analysis unit including a bottom side and a top side, the bottom side including a gas emissions sensing unit and the top side containing a data analysis and display unit;
   wherein the gas emissions sensing unit is programmed to detect gas emissions that are emitted by the biological samples; and
   wherein affixing the data collection and analysis unit to the biological sample chamber creates a single sampling atmosphere, the single sampling atmosphere preventing the entry or exit of gases and in which the gas emissions sensing unit is configured to detect gases as the gases initially contact the gas emissions sensing unit as the gases are emitted directly from the one or more biological samples and diffuse as molecules in the biological sample chamber, the molecules having unimpeded access from the biological sample to the gas emissions sensing unit.

2. The portable reusable biological sample analysis device of claim 1, wherein the biological sample chamber has an open top having a plurality of ridges and wherein the bottom side of the data collection and analysis unit has a plurality of ridges and a seal, and wherein the plurality of ridges on the biological chamber interlock with the plurality of ridges on the data collection and analysis unit.

3. The portable reusable biological sample analysis device of claim 1, wherein the gas emissions sensing unit includes an infrared sensor that is coupled to a sensor circuit board;
   and where the infrared sensor detects gas emission data that are emitted by the biological sample and the sensor circuit board is programmed to receive and transmit the gas emission data.

4. The portable reusable biological sample analysis device of claim 3, wherein the infrared sensor is a nondispersive infrared sensor.

5. The portable reusable biological sample analysis device of claim 3, wherein data analysis and display unit includes a display and an analysis circuit board that is connected to the display, the display and analysis circuit board being connected to the sensor circuit board so as to receive gas emission data from the sensor circuit board, the display and analysis circuit board further calculating respiration rates and displaying the respiration rates on the display.

6. The portable reusable biological sample analysis device of claim 5, wherein the display and analysis circuit board has an external communication link that is connected to a user interface device and wherein the display and analysis circuit board transmits and receives data to and from the user interface device.

7. The portable reusable biological sample analysis device of claim 3, wherein a temperature sensor that measures temperature data is affixed to the gas emissions sensing unit and wherein the sensor circuit board reads and transmits the temperature data.

* * * * *